(12) United States Patent
Hess et al.

(10) Patent No.: US 9,721,774 B2
(45) Date of Patent: Aug. 1, 2017

(54) INTERFACE FOR ION SOURCE AND VACUUM HOUSING

(71) Applicant: Micromass UK Limited, Wilmslow (GB)

(72) Inventors: Anthony Hess, Cheshire (GB); Steve O'Brien, Manchester (GB); Ian Trivett, Cheadle (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/023,099

(22) PCT Filed: Sep. 17, 2014

(86) PCT No.: PCT/GB2014/052815
§ 371 (c)(1),
(2) Date: Mar. 18, 2016

(87) PCT Pub. No.: WO2015/040383
PCT Pub. Date: Mar. 26, 2015

(65) Prior Publication Data
US 2016/0233074 A1    Aug. 11, 2016

(30) Foreign Application Priority Data

Sep. 20, 2013 (EP) .................................... 13185448
Sep. 20, 2013 (GB) .................................... 1316777.0

(51) Int. Cl.
*H01J 49/02* (2006.01)
*H01J 49/00* (2006.01)
(Continued)

(52) U.S. Cl.
CPC ............ *H01J 49/02* (2013.01); *G01N 27/622* (2013.01); *H01J 49/0013* (2013.01);
(Continued)

(58) Field of Classification Search
None
See application file for complete search history.

(56) References Cited

U.S. PATENT DOCUMENTS 3,418,513 A    12/1968   Elliott
4,209,696 A    6/1980    Fite
(Continued)

FOREIGN PATENT DOCUMENTS

JP    5998448    6/1984

*Primary Examiner* — Jack Berman
(74) *Attorney, Agent, or Firm* — Diederiks & Whitelaw, PLC

(57) ABSTRACT

A mass spectrometer or ion mobility spectrometer is disclosed comprising: an ion block for receiving ions; a heater for heating the ion block; a vacuum housing; and an interface block arranged between the ion block and the vacuum housing; wherein the interface block is formed from a polymer. The polymer interface block inhibits the heat transfer from the ion block to the vacuum housing and also electrically isolates the ion block and vacuum housing. The interface block further comprises at least one conduit through the body of the interface block. This enables gas to be transmitted through the interface block to the ion block, and also enables the interface block to be cooled.

21 Claims, 8 Drawing Sheets

(51) Int. Cl.
*H01J 49/04* (2006.01)
*H01J 49/10* (2006.01)
*G01N 27/62* (2006.01)

(52) U.S. Cl.
CPC ........ *H01J 49/0031* (2013.01); *H01J 49/044* (2013.01); *H01J 49/049* (2013.01); *H01J 49/10* (2013.01)

(56) References Cited

U.S. PATENT DOCUMENTS

| | | | |
|---|---|---|---|
| 4,546,253 A | 10/1985 | Tsuchiya et al. | |
| 5,170,052 A * | 12/1992 | Kato | H01J 49/045 250/281 |
| 5,485,016 A | 1/1996 | Irie et al. | |
| 5,838,002 A | 11/1998 | Sheehan | |
| 5,969,351 A | 10/1999 | Nabeshima et al. | |
| 7,098,452 B2 | 8/2006 | Schneider et al. | |
| 7,989,760 B2 * | 8/2011 | Schroeder | H01J 49/04 250/281 |
| 8,039,795 B2 * | 10/2011 | Mordehai | H01J 49/167 250/281 |
| 8,389,934 B2 | 3/2013 | Dzepina et al. | |
| 2016/0327527 A1 * | 11/2016 | Umeda | H01J 49/06 |

\* cited by examiner

INTERFACE FOR ION SOURCE AND VACUUM HOUSING

CROSS REFERENCE TO RELATED APPLICATIONS

This application is the National Stage of International Application No. PCT/GB2014/052815, filed 17 Sep. 2014 which claims priority from and the benefit of United Kingdom patent application No. 1316777.0 filed on 20 Sep. 2013 and European patent application No. 13185448.1 filed on 20 Sep. 2013. The entire contents of these applications are incorporated herein by reference.

BACKGROUND OF THE PRESENT INVENTION

The present invention relates to a spectrometer and a method of spectrometry. In particular the present invention relates to a spectrometer having a heated ion block.

In order to design an efficient source which can handle a range of solvent flow rates for desolvation it is normal to use electrical heaters to heat both the desolvation gas flow and also maintain the source ion block at a constant temperature of approximately 150° C. The amount of heat required for desolvation will depend on user input parameters and the composition and level of sample liquid flow into the source. The electrical heaters that heat the desolvation gas flow are able to be operated at temperatures up to 600° C.

It is desired provide and improved mass spectrometer or ion mobility spectrometer and an improved method of spectrometry.

SUMMARY OF THE PRESENT INVENTION

From a first aspect the present invention provides a mass spectrometer or ion mobility spectrometer comprising:
an ion block for receiving ions;
a heater for heating the ion block;
a vacuum housing; and
an interface block arranged between the ion block and the vacuum housing;
wherein the interface block is formed from a polymer;
wherein the interface block comprises an axial conduit extending through it for allowing ions to pass from the ion block into the vacuum housing; and
wherein the interface block further comprises at least one conduit through the body of the interface block for transmitting gas through the interface block to the ion block.

The ion block is heated by the heater in use and the provision of the polymer interface block inhibits heat transfer from the heated ion block to the vacuum housing. This keeps the heat contained in the source region, where it is required, and stops the flow of heat to other areas of the instrument, which would otherwise present functional problems and drive up the power consumption via dissipated heat loss. For example, the vacuum housing may house an ion analyser and it may be desired to limit the heat transfer from the ion block to the analyser. The body of the interface block comprises at least one conduit for transmitting gas. This enables gas to be passed through the interface block so as to cool the interface block and further reduce heat transfer between the heated ion block and the vacuum housing. This arrangement also enables desired gases to be supplied to the ion block without having to make external gas connections to the ion block.

The polymer interface block also provides a convenient and simply way to electrically isolate the ion block from the vacuum housing, since it is desirable to maintain the ion block at a different electrical potential to the vacuum housing.

Preferably, the ion block is mounted to one side of the interface block. Additionally, or alternatively, the vacuum housing may be mounted to one side of the interface block. Preferably, the ion block is mounted to one side of the interface block and the vacuum housing is mounted to the opposing side of the interface block.

The interface block is preferably configured to connect the ion block to the vacuum housing in a gas tight manner.

Preferably, the polymer interface block is arranged and configured to thermally insulate the vacuum housing from the ion block. The material forming the interface block preferably has a thermal conductivity of <0.7 W/m.° C.; <0.6 W/m.° C.; <0.5 W/m.° C.; <0.4 W/m.° C.; <0.3 W/m.° C.; <0.2 W/m.° C.; or <0.1 W/m.° C. The material forming the interface block preferably has a thermal conductivity in the range of 0.01 to 0.5 W/m.° C.

Preferably, the polymer interface block is arranged and configured to electrically isolate the ion block from the vacuum housing.

The interface block may be at least x % by weight polymer, wherein x is selected from the group consisting of: >70; >75; >85; >90; and >95.

The polymer is preferably a thermal insulator. The polymer is preferably an electrical isolator. The polymer is preferably chemically stable and so is resistant to chemical attack from chemicals generated by an ion source of the spectrometer.

The vacuum housing preferably comprises at least one of the following: ion optics; an ion mass analyser; an ion mobility analyser; or an ion trap.

A vacuum pump is preferably connected to the vacuum housing for evacuating the housing to a pressure below the ambient pressure. The ion source is preferably an atmospheric pressure ion source, although lower pressure ion sources are contemplated herein.

Preferably, the vacuum housing and/or the ion block is substantially formed from metal. The metal of the vacuum housing is preferably aluminium. The metal of the ion block is preferably stainless steel.

The ion block preferably comprises an electrical heater for heating the ion block. Electronics for powering the heater may pass through a conduit in the interface block to the heater.

At least one conduit is provided through the body of the interface block for transmitting gas through the interface block to the ion block. The vacuum housing may comprise at least one conduit through its body for supplying gas to the at least one conduit in the interface block and/or the ion block may comprise at least one conduit for receiving gas from the conduit in the interface block. Such conduits may be used to supply gas to the ion block such that the gas exits the ion block in a counter-flow to the motion of ions into a sampling orifice in the ion block. This gas flow prevents contaminants from entering the ion block. An electric field may be provided for causing ions to enter the ion block against the flow of the gas.

The heater source in the ion block is preferably an electric heater and the spectrometer comprises a power cable for transmitting power to the electric heater. The power cable preferably extends through a conduit through the body of the interface block.

The interface block preferably has an axial conduit extending through it for allowing ions to pass from the ion block to the vacuum housing. An ion guide is preferably arranged in the axial conduit for guiding the ions. The ion guide is formed from electrodes and may take the form of a multipole ion guide or an ion tunnel ion guide formed from a plurality of apertured electrodes. Alternative types of ion guides may be used.

The spectrometer preferably further comprises a source enclosure having a cavity therein which houses an ion source. The source enclosure is preferably mounted to the interface block such that the cavity is arranged over and encloses the ion block. The source enclosure preferably includes an ESI probe, although other types of ion source are also contemplated herein.

The inner surface of the cavity is preferably metallic. For example, the inner surface may be aluminium. The outer surface of the source enclosure is preferably formed from a plastic cover. This plastic cover may serve to provide heat and/or electric insulation so as to protect the operator. The cover may be vented to the ambient environment. This helps maintain a constant temperature of the source enclosure or source chamber.

The source enclosure is preferably mounted to the interface block such that the metallic inner surface of the source enclosure is spaced apart from the vacuum housing by the interface block. This serves to substantially thermally insulate the source enclosure from vacuum housing. Mechanical screws may extend through the outer perimeter of the interface block in order to connect the source enclosure with the vacuum housing. These screws may provide an electrically grounded connection between the source enclosure and the vacuum housing. These screws may enable a minimal amount of heat transfer between the source enclosure and the vacuum housing, although the polymer interface block is considered to substantially thermally insulate the source enclosure from the vacuum housing.

A polymer buffer element is preferably mounted to the ion block and arranged and configured to engage an inner surface of the source enclosure cavity so as to space the inner surface of the source enclosure from the ion block. The buffer element serves to thermally and/or electrically isolate the ion block from the source enclosure.

The interface block may comprises a groove or handle for use in removing the interface block from the vacuum housing.

The spectrometer preferably comprises a miniature mass spectrometer.

From a second aspect the present invention also provides a method of mass spectrometry or ion mobility spectrometry comprising:
  providing a spectrometer as described herein:
  heating the ion block with said heater.
  transmitting ions from said ion block, through said axial conduit in said interface block and into said vacuum housing; and
  analysing said ions with an analyser arranged in said vacuum housing.

The method preferably comprises supplying a gas to the ion block through said at least one conduit in the body of the interface block.

The method preferably comprises supplying said gas through at least one conduit in the body of said vacuum housing and into said at least one conduit in the interface block; and/or receiving said gas from said at least one conduit in the interface block in at least one conduit within the ion block.

The method preferably comprises: using the polymer interface block to thermally insulate a high temperature component on one side of the interface block from a low temperature component on the opposite side of the interface block; and/or using the polymer interface block to electrically insulate a high voltage component on one side of the interface block from a low voltage component on the opposite side of the interface block.

The method preferably comprises guiding ions through said axial conduit in an ion guide formed from electrodes.

According to an embodiment the spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

As described above, the interface block most preferably comprises at least one conduit through the body of the interface block for transmitting gas through the interface block to the ion block. However, less preferably, the interface block may not have such a gas conduit.

Accordingly, the present invention also provides a mass spectrometer or ion mobility spectrometer comprising:

an ion block for receiving ions;

a heater for heating the ion block;

a vacuum housing; and an interface block arranged between the ion block and the vacuum housing;

wherein the interface block is formed from a polymer.

The spectrometer may comprise any one, or any combination of any two or more, of the features described above in relation to the first aspect of the present invention.

The present invention also provides a method of mass spectrometry or ion mobility spectrometry comprising:

providing a spectrometer as claimed in described above:

heating the ion block with said heater.

transmitting ions from said ion block, through said interface block and into said vacuum housing; and analysing said ions with an analyser arranged in said vacuum housing.

The method may comprise any one, or any combination of any two or more, of the features described above in relation to the second aspect of the present invention.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1A:
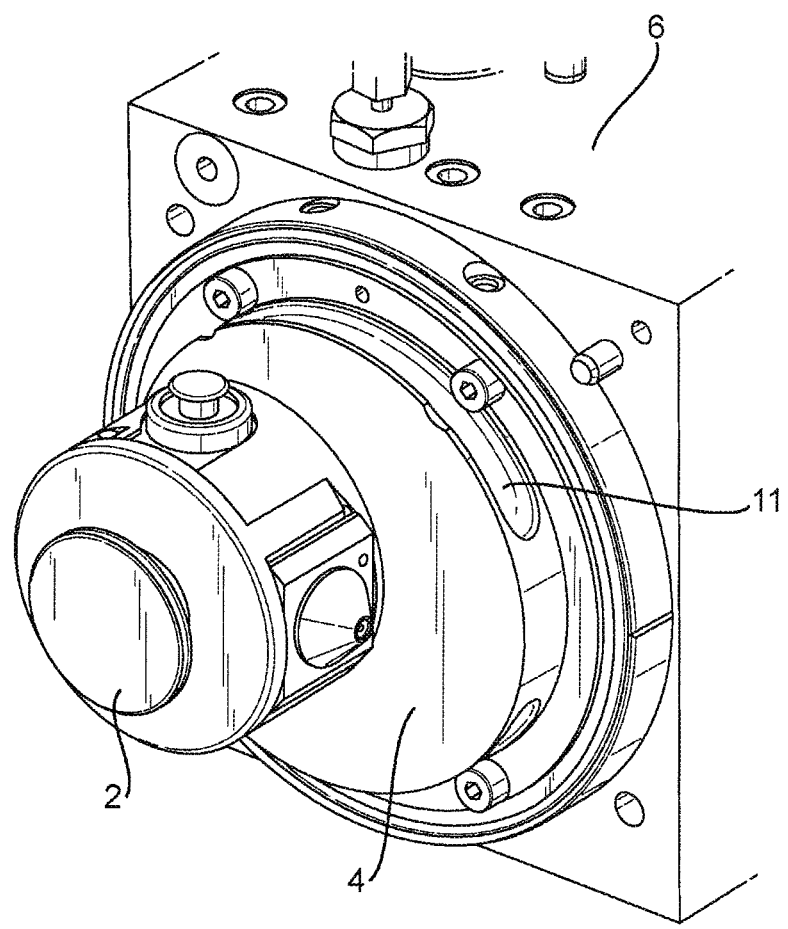
FIG. 1A shows a perspective view of part of a mass spectrometer comprising an ion block, a pumping block and a vacuum housing.
Figure 1B:
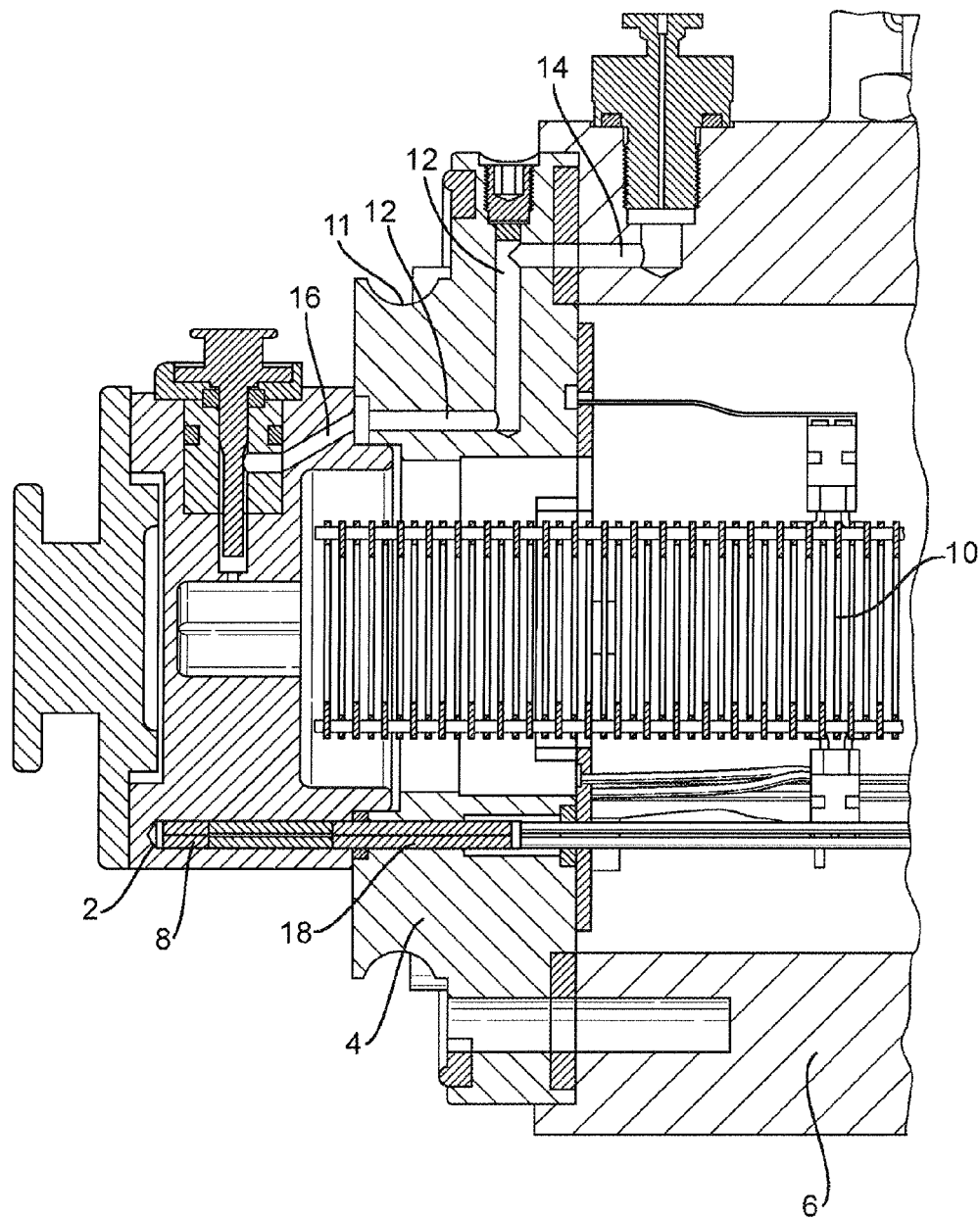
FIG. 1B shows a cross-sectional view through the same part of the mass spectrometer.

FIG. 1A shows a perspective view of part of a mass spectrometer comprising an ion block 2, an interface block (referred to herein as a pumping block) 4 and vacuum housing 6 for housing an ion analyser. FIG. 1B shows a cross-sectional view through the same part of the mass spectrometer.

The ion block 2 is formed from metal and comprises a sampling cone for sampling ions and transmitting them downstream into the vacuum housing 6. The ion block 2 comprises an electrical heat source 8 for heating the ion block 2 to the desired temperature.

The vacuum housing 6 houses an ion analyser and provides a vacuum chamber around the analyser. A vacuum pump is provided to forming the vacuum in the housing 6. FIG. 1B shows an ion guide 10 extending from the pumping block 4 into the vacuum housing 6 for guiding ions from the ion block 2 into the vacuum housing 6.

The pumping block 4 forms an interface between the ion block 2 and the wall of the vacuum housing 6. The pumping block 4 comprises a groove 11 in its circumferential surface that acts as a handle for removing the pumping block 4 from the vacuum housing 6. The pumping block 4 supports ion guide lenses 10 for guiding ions received from the ion block 2, through the pumping block 4 and into the vacuum housing 6. Internal drillings are also provided in the pumping block 4 in order to form conduits 12 through the body of the pumping block 4 so that gases can be delivered through the pumping block 4 to the required location. In the embodiment shown in FIG. 1B, a gas conduit 14 is also formed in the body of the vacuum housing 6 for supplying gas to the conduit 12 in the pumping block 4. A gas conduit 16 is also formed in the ion block 2 for receiving gas from the conduit 12 in the pumping block 4.

A conduit 18 is provided through the pumping block 4, between the ion block 2 and the vacuum housing 6 so as to enable the electronics for powering the electrical heater 8 in the ion block 2 to pass from the vacuum housing 6, through the pumping block 4 and to the electrical heater 8 in the ion block 2.

The ion block 2 is preferably heated to approximately 150° C. during continuous use. This is achieved by the electrical heater 8 in the ion block 2, which is preferably a cartridge heater. Residual heat from the desolvation heated gas flow also contributes to heating the ion block 2. The lower the power required for heating the ion block 2, the better the overall power consumption of the instrument.

The ion block 2 is preferably maintained at a constant voltage +150 V and is desired to be electrically insulated from the analyser.

Figure 2A:
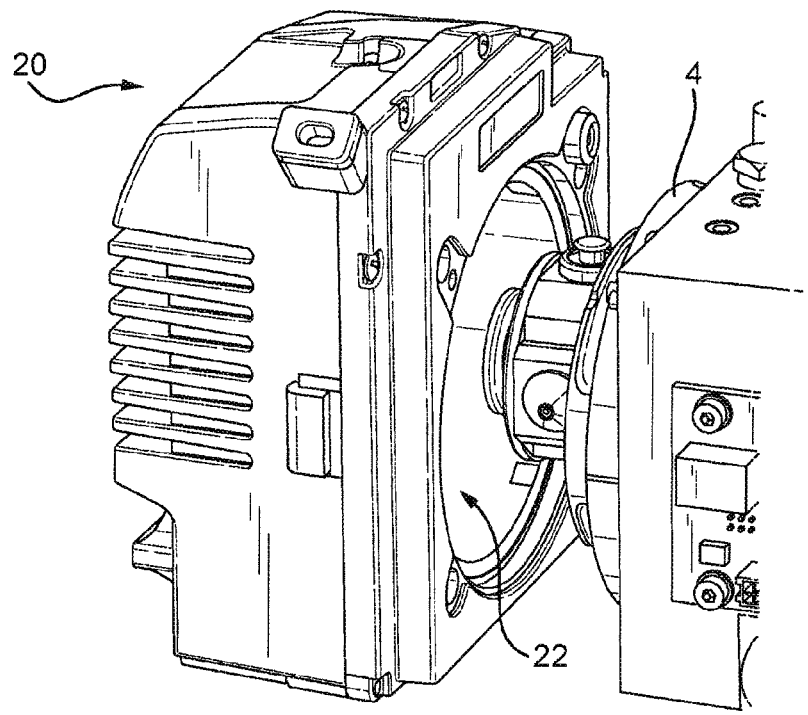
FIGS. 2A to 2C show different views of an ion source enclosure being mounted over the ion block and onto the pumping block.
Figure 2B:
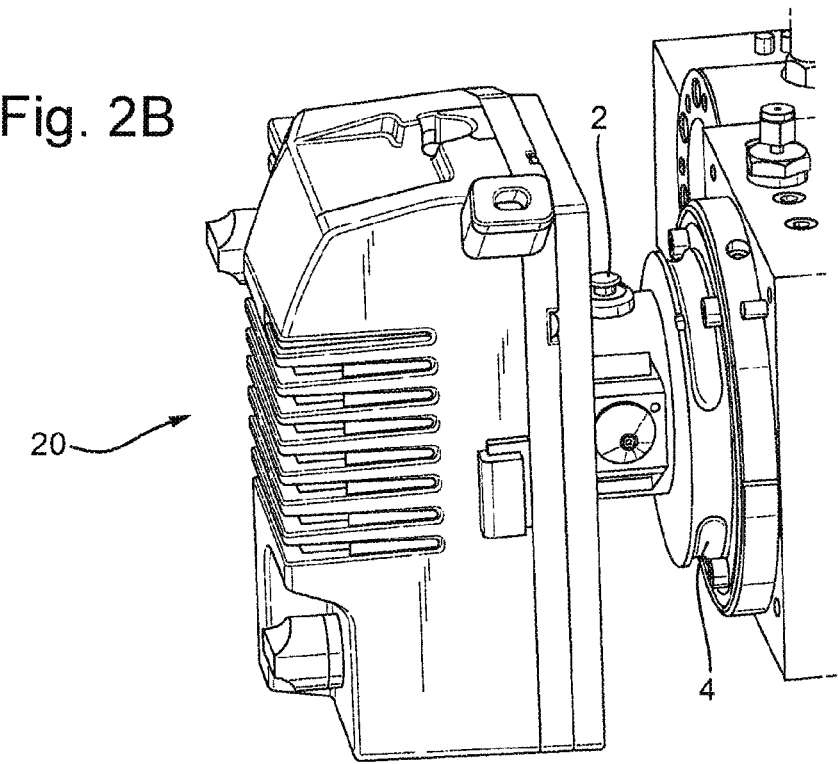
Figure 2C:
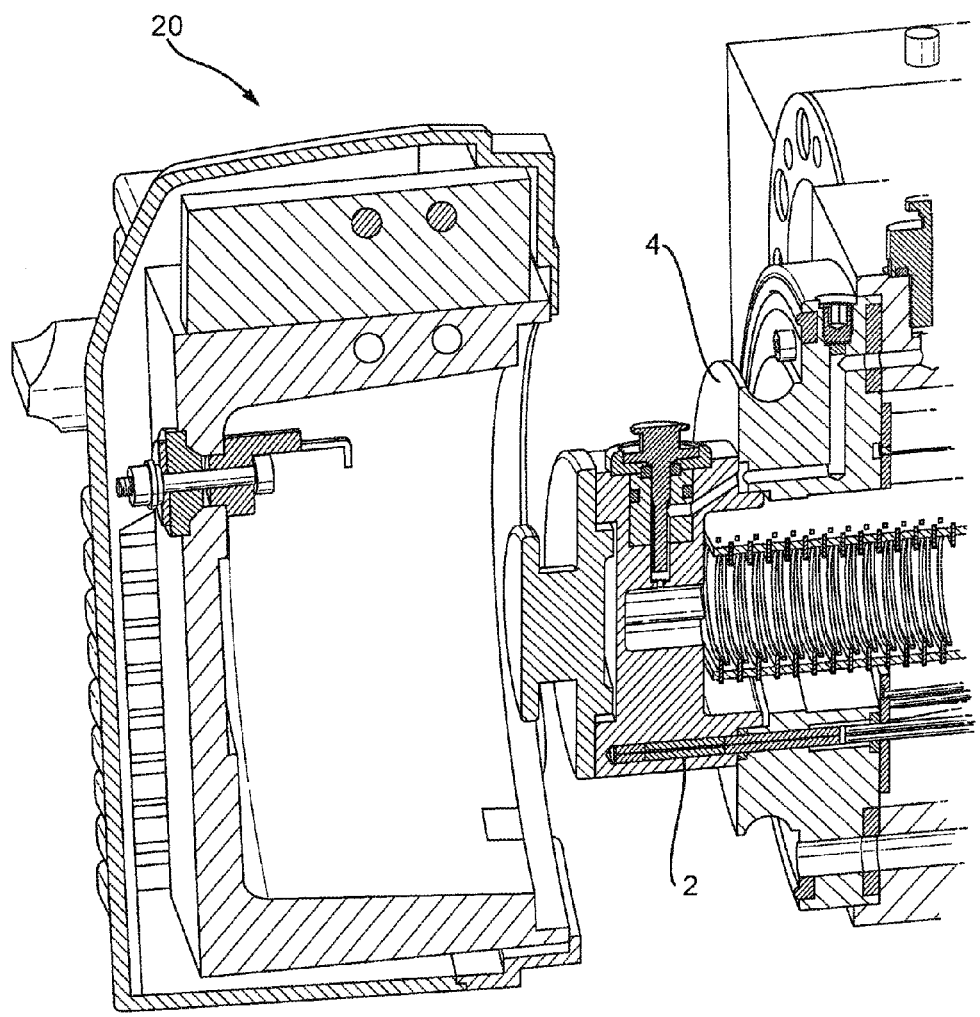

FIGS. 2A to 2C show two perspective views and a cross-sectional view of a source enclosure 20 being fitted over the ion block 2 and onto the pumping block 4. The source enclosure 20 comprises an enclosure 22 that is open at one end for connecting it to the pumping block 4. The inner surface of the source enclosure 20 is formed from aluminium and provides an enclosed region in which the ESI process takes place in order to ionise the analyte. The outer surface of the source enclosure 20 is covered with a plastic cover, which directs enough air flow from the machine front covers to maintain a consistent and acceptable source temperature. The plastic cover also serves to protect the user from the hot aluminium surfaces of the source enclosure 20.

Figure 3A:
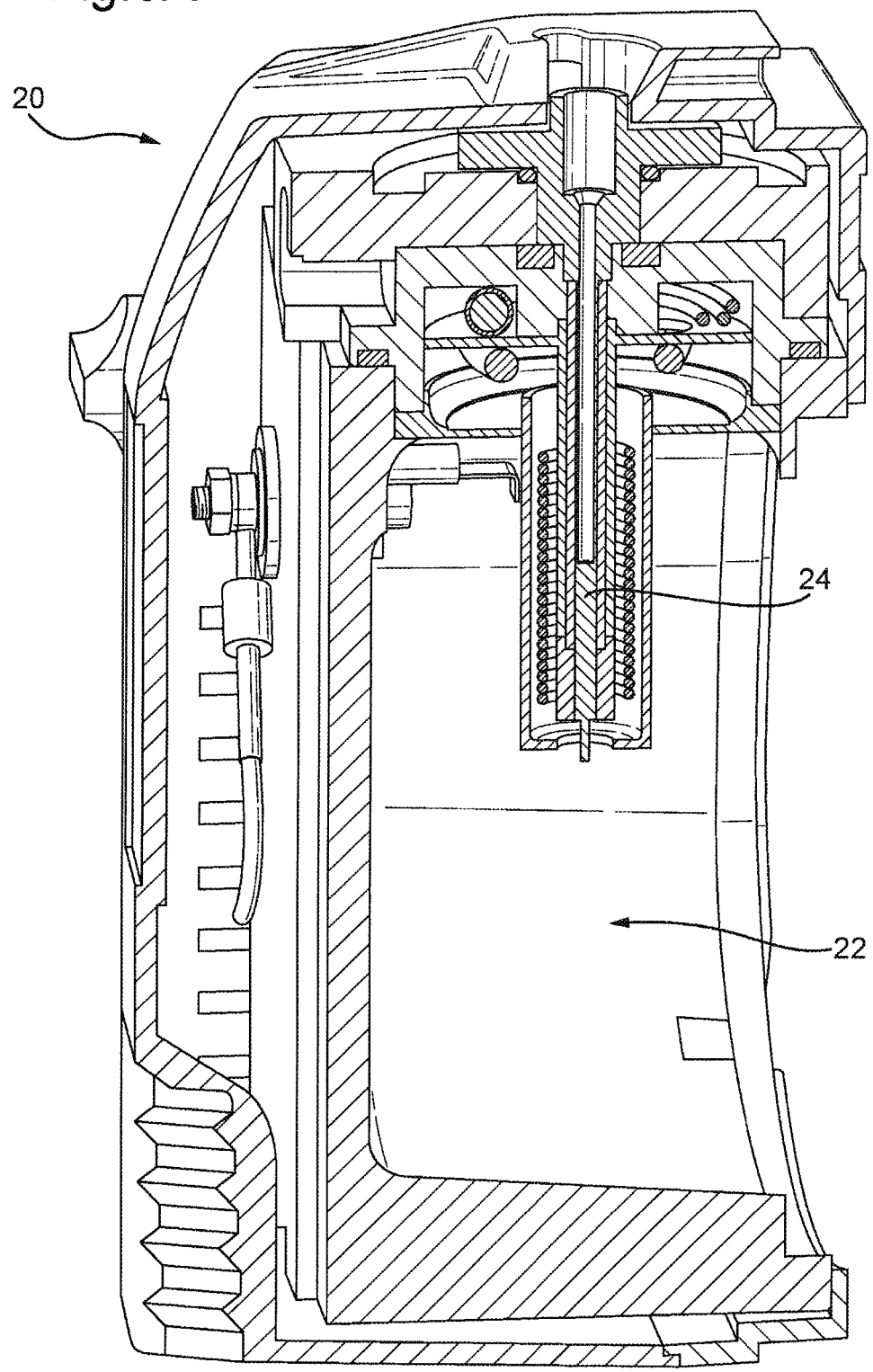
FIG. 3A shows a cross-sectional view of the ion source enclosure.

FIG. 3A shows a cross sectional view through the source enclosure 20 taken through a different plane to that in FIG. 2C. In the view of FIG. 3A, the nebuliser tube 24 in which the ESI spray probe can be inserted is seen extending into the cavity 22 of the source enclosure 20. The nebuliser tube 24 and spray probe comprise concentric conduits that transmit nebuliser gas and analyte solution. The nebuliser gas helps to convert the analyte solution into charged droplets. The apparatus also comprises a conduit for conveying desolvation gas to the end of the probe and a heater for heating the desolvation gas. The desolvation gas helps to evaporate the solvent in the sprayed droplets so as to produce desolvated ions. An electric field causes the resulting ions to enter the ion block 2 thorough the sampling orifice. A counter gas flow in a direction opposite to the motion of the ions may be generated (i.e. in a direction out of the sampling orifice) in order to prevent contaminants entering the sampling orifice and ion block.

Figure 3B:
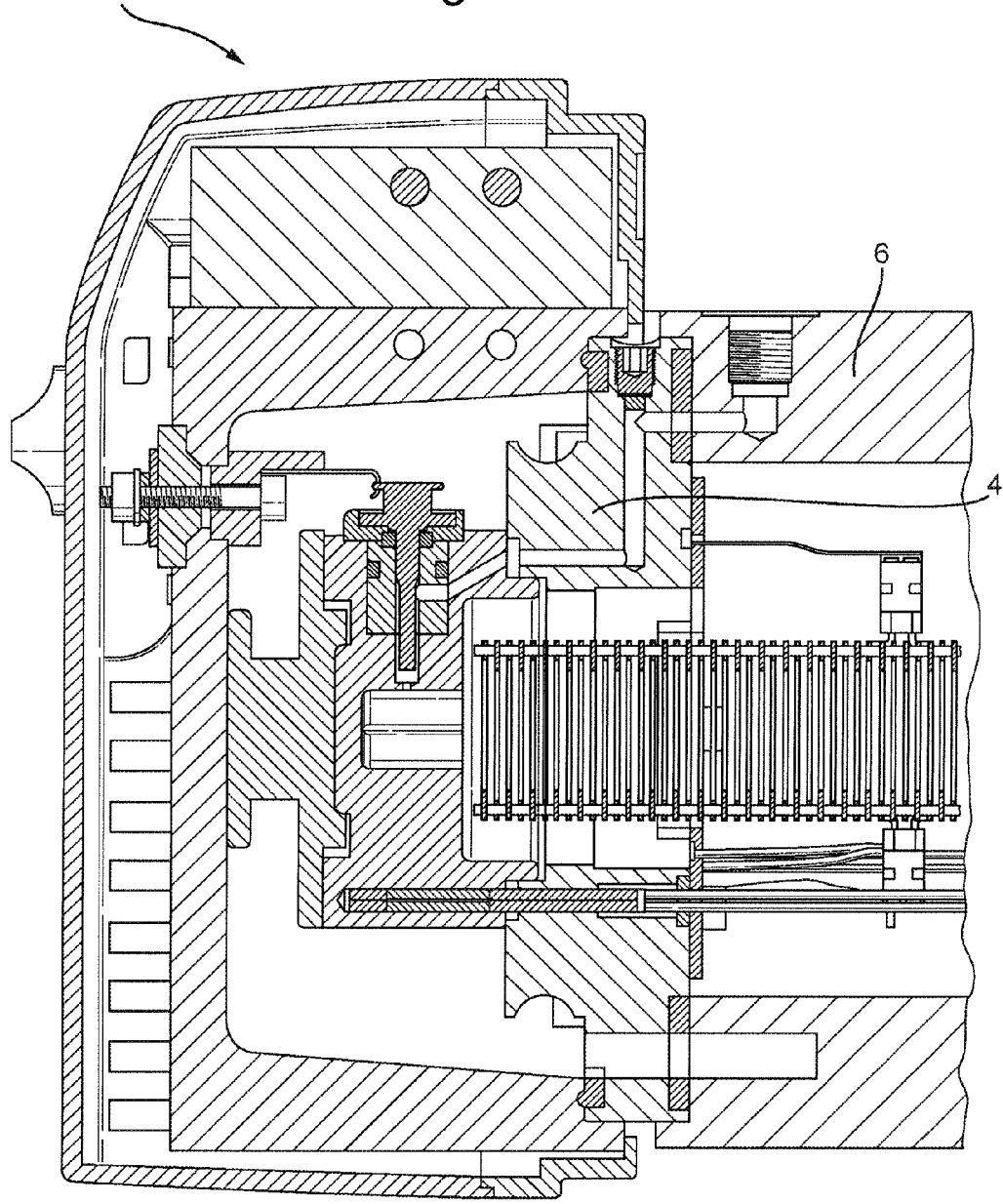
FIG. 3B shows a cross-sectional view of the ion source enclosure mounted on the pumping block.

FIG. 3B shows a cross-sectional view of the arrangement once the source enclosure 20 has been fitted onto the pumping block 4. The pumping block 4 is exposed to both hot gases and chemical substances from the ESI probe tip.

The pumping block 4 is preferably formed of PEEK and so is able to perform a number of functions. The pumping block 4 is able to mechanically support the geometry of the components and also withstand contact with hot gases and chemicals from the ESI probe tip. The pumping block 4 is a thermal insulator and so limits heat passing from the ion block 2 to the vacuum housing 6. The dielectric properties of the pumping block 4 are sufficient to electrically isolate the ion block 2 from the vacuum housing 6 and hence further electrical insulators are not required to perform this function. The pumping block 4 eliminates direct component contact between the source enclosure 20 and the vacuum housing 6, also providing thermal and electrical isolation from the ion block 2. The thermal properties of the PEEK have been used to minimise the thermal conduction through the assembly.

Figure 4A:
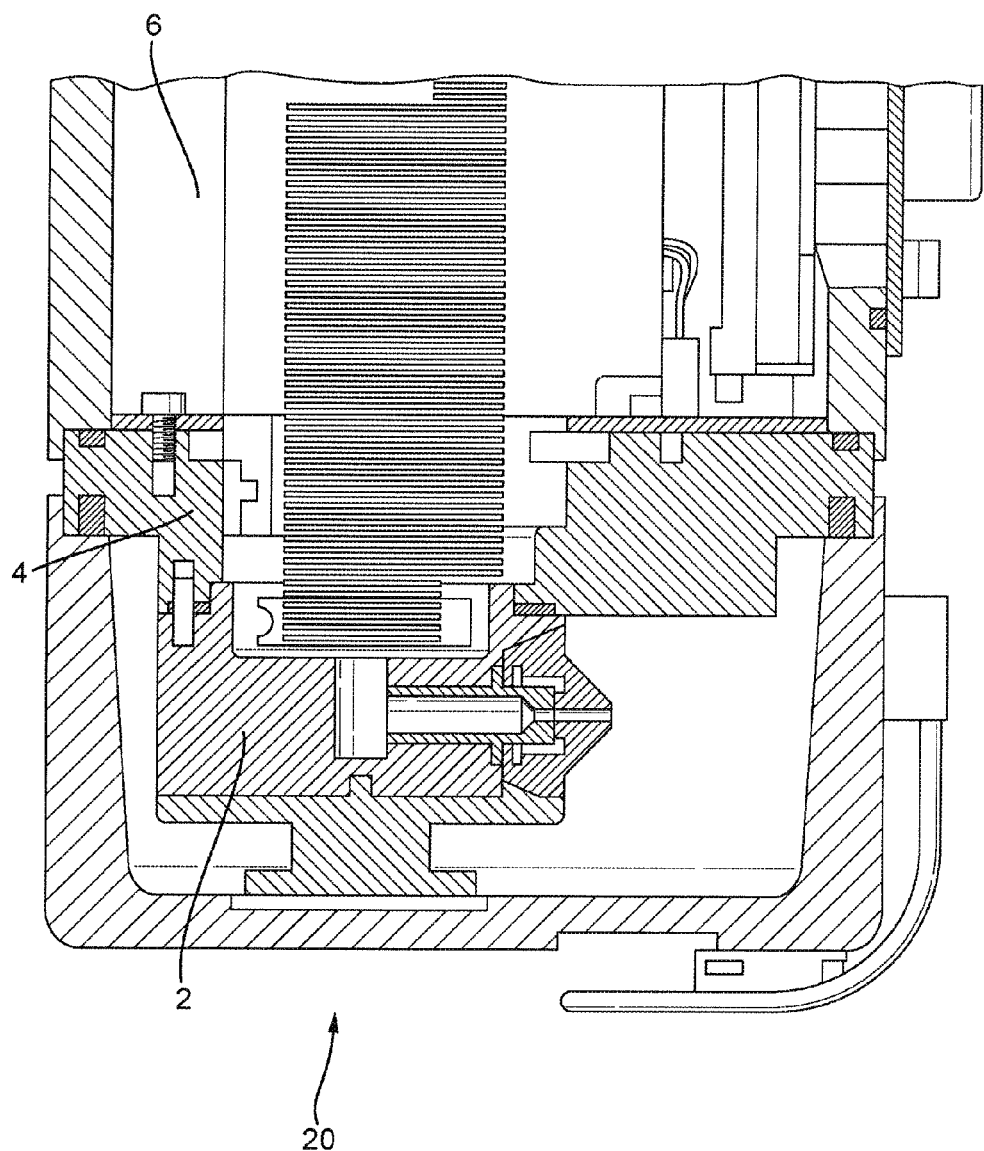
FIG. 4A shows another cross-sectional view of the ion source enclosure mounted on the pumping block.

FIG. 4A shows the ion block 2 mechanically fixed to the pumping block 4, which is in turn connected to the vacuum housing 6. In use, the ion block 2 is maintained at a constant temperature. The vacuum housing 6 has a large thermal mass relative to the ion block 2 and tends to act as a heat sink fixed at a constant temperature, generally a few degrees above ambient. However, the thermal properties of the pumping block 4 minimise the amount of heat conducted to the analyser. Simple calculations can be used to model the effect that the geometry and material of the pumping block 4 have on the heat transfer.

Figure 4B:
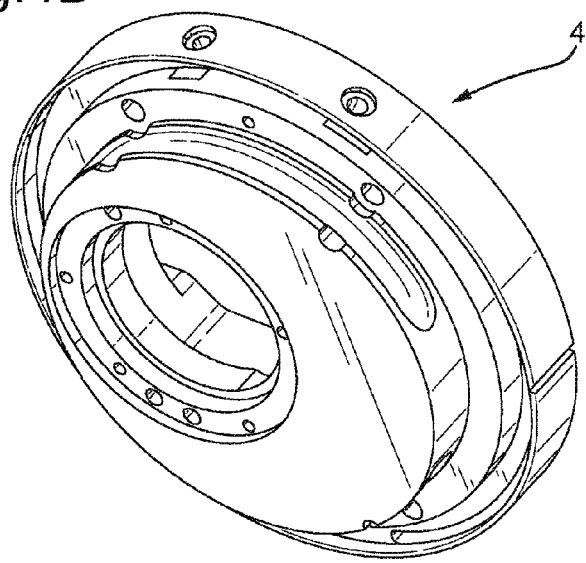
FIG. 4B shows a perspective view of the pumping block.
Figure 4C:
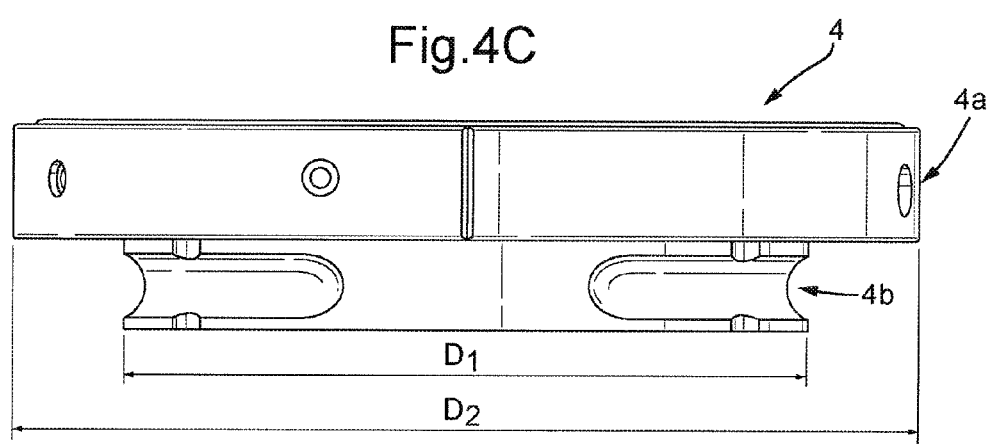
FIG. 4C shows a side view of the pumping block and FIG. 4D shows a cross-sectional view of the pumping block.
Figure 4D:
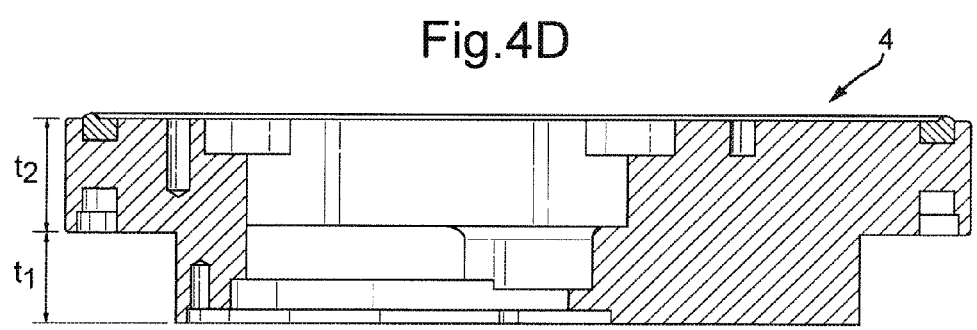

FIG. 4B shows a perspective view of the pumping block 4 of the preferred embodiment, FIG. 4C shows a side view of the pumping block 4 and FIG. 4D shows a cross-sectional view through the pumping block 4. The pumping block 4 is essentially formed from two co-axial, annular portions $4a,4b$. In order to build a simple thermal model of the pumping block 4, the pumping block 4 is considered to have a simplified geometry formed from two co-axial, cylindrical portions $4a,4b$ having the diameters and thicknesses shown in FIGS. 4C and 4D, and having the same conductivity, k. The combined thermal resistance of the pumping block $R_{pb}$ can be considered to equate to the sum of the thermal resistances $R_1$ and $R_2$ of the two cylindrical portions 4a,4b. The thermal resistance of the pumping block 4 can therefore be expressed by the following equation:

$$R_{pb} = R_1 + R_2 = \frac{4(D_2^2 t_1 + D_1^2 t_2)}{k\pi D_1^2 D_2^2} = \frac{\Delta T}{P} = \frac{\Delta t}{kA}$$

where $R_1$ is the thermal resistance of the first cylindrical portion 4a, $R_2$ is the thermal resistance of the second cylindrical portion 4b, $D_1$ is the diameter of the first cylindrical portion 4a, $t_1$ is the thickness of the first cylindrical portion 4a, $D_2$ is the diameter of the second cylindrical portion 4b, $t_2$ is the thickness of the second cylindrical portion 4b, k is the thermal conductivity of the material forming the pumping block 4, $\Delta T$ is the difference in temperature across the pumping block 4, P is the power required to maintain the temperature difference across the pumping block 4, $\Delta t$ is the thickness of the pumping block 4, and A is the cross-sectional area of the pumping block 4.

The above equation can be used to determine that amount of power that is required in order to maintain a fixed temperature difference across the pumping block 4. Assuming that the pumping block 4 is made from PEEK (k=0.29 W/m.° C.), has a diameter $D_1$ of 77 mm, a thickness $t_1$ of 13 mm, a diameter $D_2$ of 102 mm, a thickness $t_2$ of 10 mm, and that it is desired to maintain the ion block side of the pumping block at 150° C. and the vacuum housing side of block at 40° C., then the power required to maintain this temperature differential is 8.5 W. This it to be compared with a power of >5 kW, if the pumping block was formed from conventional material such as aluminium. It will be appreciated that even if a pumping block material with a conductivity of 1 W/m.° C. was used, this would require a power increase of 27 W relative to a pumping block formed from PEEK.

The thicknesses $t_1$ and $t_2$ of the pumping block portions 4a,4b in the above embodiment were selected in order to provide mechanical strength and also to provide a relatively high thermal resistance. If the overall thickness of the pumping block 4 was reduced by 50% this would still provide the required rigidity, but would increase the power requirement to maintain the temperature difference across the pumping block 4 by 100%.

Although the pumping block 4 has been described above as being formed from PEEK, it is contemplated that polymer materials other than PEEK could be used to provide relatively high thermal resistance. The material forming the pumping block (i.e. interface block) of the present invention preferably has a thermal conductivity in the range of 0.01 to 0.5 W/m.° C.

Polymers which are also electrical isolators are preferred. Polymers which are resistant to chemical attack and have chemical stability are particularly preferred. Polymers which have vacuum compatibility are preferred so as to prevent out-gassing from the polymer under vacuum conditions.

As described above, the preferred embodiment reduces the overall power required to heat functioning components in the source region by minimising thermal conduction into the vacuum housing 6. The pumping block 4 also couples as the gas sealing wall of the vacuum chamber 6 and hence reduces the component count and simplifies the instrument.

Current pumping blocks are aluminium and have mechanical features built into the design to reduce the amount of direct surface contact, and hence thermal conduction, between the ion block and vacuum housing. However, these pumping blocks do not prevent heat transfer through the faces of the pumping block.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer or ion mobility spectrometer comprising:
   an ion block for receiving ions;
   a heater for heating the ion block;
   a vacuum housing; and
   an interface block arranged between the ion block and the vacuum housing;
   wherein the interface block is formed from a polymer;
   wherein the interface block comprises an axial conduit extending through it for allowing ions to pass from the ion block into the vacuum housing; and
   wherein the interface block further comprises at least one conduit through the body of the interface block for transmitting gas through the interface block to the ion block.

2. The spectrometer of claim 1, wherein the ion block is mounted to one side of the interface block and/or the vacuum housing is mounted to an opposing side of the interface block.

3. The spectrometer of claim 1, wherein the vacuum housing comprises at least one conduit through its body for supplying gas to said at least one conduit in the interface block and/or wherein the ion block comprises at least one conduit for receiving gas from said at least one conduit in the interface block.

4. The spectrometer of claim 1, wherein the polymer interface block is arranged and configured to thermally insulate the vacuum housing from the ion block.

5. The spectrometer of claim 1, wherein the material forming the interface block has a thermal conductivity selected from the group consisting of: <0.7 W/m.° C.; <0.6 W/m.° C.; <0.5 W/m.° C.; <0.4 W/m.° C.; <0.3 W/m.° C.; <0.2 W/m.° C.; <0.1 W/m.° C.; or 0.01 to 0.5 W/m.° C.

6. The spectrometer of claim 1, wherein the interface block is formed from PEEK.

7. The spectrometer of claim 1, wherein the polymer interface block is arranged and configured to electrically isolate the ion block from the vacuum housing.

8. The spectrometer of claim 1, wherein an ion guide formed from electrodes is arranged in said axial conduit for guiding ions.

9. The spectrometer of claim 1, wherein the vacuum housing comprises at least one of the following: ion optics; an ion mass analyser; an ion mobility analyser; or an ion trap.

10. The spectrometer of claim 1, wherein the vacuum housing and/or the ion block is substantially formed from metal.

11. The spectrometer of claim 1, further comprising an ion source enclosure having a cavity therein which houses an ion source, wherein the source enclosure is mounted to the interface block such that the cavity is arranged over and encloses the ion block.

12. The spectrometer of claim 11, wherein the inner surface of said cavity is metallic and wherein the source enclosure is mounted to the interface block such that the metallic inner surface is spaced apart from the vacuum housing by the interface block.

13. The spectrometer of claim 11, wherein a polymer buffer element is mounted to the ion block and arranged and configured to engage an inner surface of the source enclosure cavity so as to space the inner surface of the source enclosure from the ion block.

14. The spectrometer of claim 1, wherein the spectrometer comprises a miniature mass spectrometer or a miniature ion mobility spectrometer.

15. The spectrometer of claim 1, wherein the interface block comprises a groove or handle for use in removing the interface block from the vacuum housing.

16. The spectrometer of claim 1, wherein electronics for powering said heater pass through a conduit in said interface block to said heater.

17. A method of mass spectrometry or ion mobility spectrometry conducted with a spectrometer comprising an ion block for receiving ions; a heater for heating the ion block; a vacuum housing; and an interface block arranged between the ion block and the vacuum housing; wherein the interface block is formed from a polymer; wherein the interface block comprises an axial conduit extending through it for allowing ions to pass from the ion block into the vacuum housing; and wherein the interface block further comprises at least one conduit through the body of the interface block for transmitting gas through the interface block to the ion block, said method comprising:

heating the ion block with said heater, transmitting ions from said ion block, through said axial conduit in said interface block and into said vacuum housing; and analysing said ions with an analyser arranged in said vacuum housing.

18. The method of claim 17, comprising supplying a gas to the ion block through said at least one conduit in the body of the interface block.

19. The method of claim 18, comprising supplying said gas through at least one conduit in the body of said vacuum housing and into said at least one conduit in the interface block; and/or receiving said gas from said at least one conduit in the interface block in at least one conduit within the ion block.

20. The method of claim 17, comprising:
using the polymer interface block to thermally insulate a high temperature component on one side of the interface block from a low temperature component on the opposite side of the interface block; and/or
using the polymer interface block to electrically insulate a high voltage component on one side of the interface block from a low voltage component on the opposite side of the interface block.

21. The method of claim 17, comprising guiding ions through said axial conduit in an ion guide formed from electrodes.

* * * * *